US012778773B2

(12) United States Patent
Boiten et al.

(10) Patent No.: US 12,778,773 B2
(45) Date of Patent: Nov. 3, 2026

(54) PROSTHETIC KNEE JOINT

(71) Applicant: OTTOBOCK SE & CO. KGAA, Duderstadt (DE)

(72) Inventors: Herman Boiten, Duderstadt (NL); Sarah Bierbaum, Duderstadt (DE); Jens Nörthemann, Duderstadt (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 747 days.

(21) Appl. No.: 18/252,055

(22) PCT Filed: Nov. 8, 2021

(86) PCT No.: PCT/EP2021/080973
§ 371 (c)(1),
(2) Date: May 8, 2023

(87) PCT Pub. No.: WO2022/101144
PCT Pub. Date: May 19, 2022

(65) Prior Publication Data

US 2023/0398002 A1 Dec. 14, 2023

(30) Foreign Application Priority Data

Nov. 10, 2020 (DE) ..................... 10 2020 129 644.4

(51) Int. Cl.
*A61F 2/64* (2006.01)
*A61F 2/74* (2006.01)

(52) U.S. Cl.
CPC ................ *A61F 2/64* (2013.01); *A61F 2/748* (2021.08)

(58) Field of Classification Search
CPC .... A61F 2/64; A61F 2/748; A61F 2002/5075; A61F 2002/6818; A61F 2/74; A61F 2/744; A61F 2/68
See application file for complete search history.

(56) References Cited

U.S. PATENT DOCUMENTS 5,376,138 A 12/1994 Bouchard et al.
5,704,945 A * 1/1998 Wagner ..................... A61F 2/64 623/44

(Continued)

FOREIGN PATENT DOCUMENTS

CN 1141157 A 6/2003
CN 101317793 A 12/2008

(Continued)

OTHER PUBLICATIONS

Apr. 29, 2026 Office Action in Corresponding Chinese Application 202180075015.2.

*Primary Examiner* — Yashita Sharma
(74) *Attorney, Agent, or Firm* — WCF IP

(57) ABSTRACT

The invention relates to a prosthetic knee joint with a joint lower part, a joint upper part and a hydraulic system with at least one switch valve, wherein the hydraulic system comprises an extension chamber, a flexion chamber and at least one piston, the movement of which causes the volume of the extension chamber and/or the flexion chamber to change, the switch chamber comprises a valve housing and a switch element movably mounted therein, which can be brought into a first position and into a second position within the valve housing and divides an interior of the valve housing into a first chamber and a second chamber, the switch element is pre-tensioned by at least one pre-tensioning element arranged in the switch valve, the prosthetic knee joint comprises at least one spring element that applies a counter-force to the switch element, which is oriented against the pre-tension, (Continued)

Figure 1:
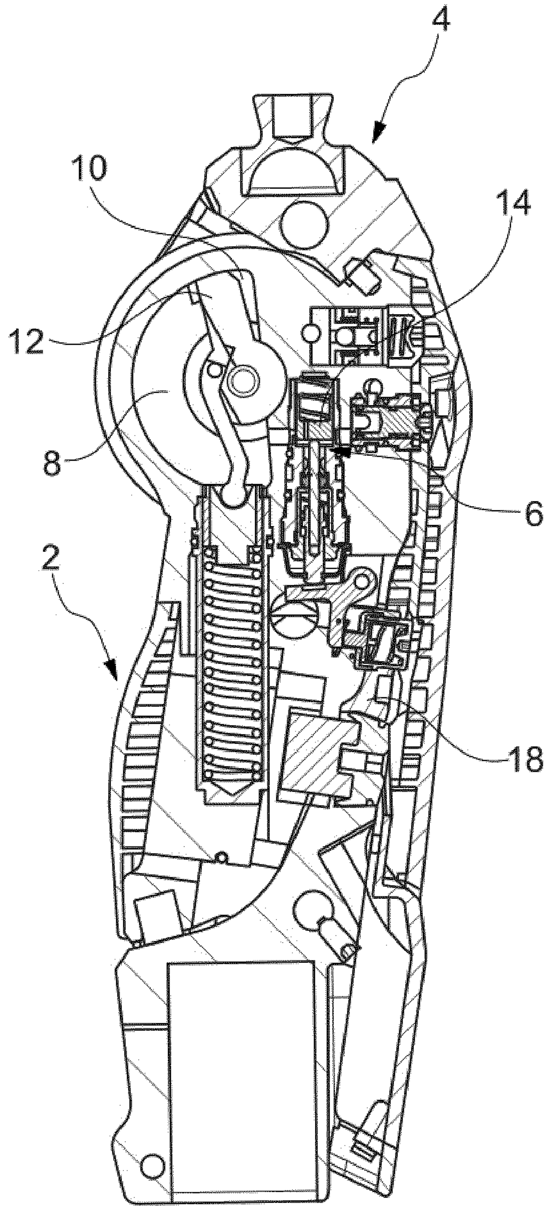

wherein, within the valve housing and/or the switch element, at least one fluid connection is arranged between the first chamber and the second chamber.

7 Claims, 5 Drawing Sheets

(56) References Cited

U.S. PATENT DOCUMENTS

| | | | |
|---|---|---|---|
| 7,883,548 | B2 | 2/2011 | Lang |
| 11,602,444 | B2 | 3/2023 | Seyr |
| 2006/0293761 | A1 | 12/2006 | Baumann et al. |
| 2021/0113354 | A1 | 4/2021 | Boiten |

FOREIGN PATENT DOCUMENTS

| | | | |
|---|---|---|---|
| CN | 101959477 | B | 8/2013 |
| CN | 104602650 | A | 5/2015 |
| CN | 110392559 | A | 10/2019 |
| CN | 111225636 | A | 6/2020 |
| DE | 195 06 426 | C1 | 11/1996 |
| DE | 693 12 771 | T2 | 12/1997 |
| DE | 10 2005 029 160 | A1 | 12/2006 |
| DE | 10 2018 111 441 | A1 | 11/2019 |
| JP | HO8317944 | A | 3/2004 |
| JP | 6110207 | B2 | 4/2017 |
| JP | 2020500568 | A | 4/2018 |
| RU | 2054906 | C1 | 2/1996 |
| RU | 2076670 | C1 | 4/1997 |
| RU | 43156 | U1 | 1/2005 |
| RU | 2480182 | C2 | 4/2013 |
| RU | 2674875 | C2 | 12/2018 |
| RU | 2678370 | C2 | 1/2019 |
| WO | 9900075 | A1 | 1/1999 |
| WO | WO2019219697 | A1 | 11/2019 |

* cited by examiner

PROSTHETIC KNEE JOINT

The invention relates to a prosthetic knee joint with a joint lower part, a joint upper part and a hydraulic system with at least one switch valve, wherein

- the hydraulic system comprises an extension chamber, a flexion chamber and at least one piston, the movement of which causes the volume of the extension chamber and/or the flexion chamber to change,
- the switch valve comprises a valve housing and a switch element movably mounted therein, which can be brought into a first position and into a second position within the valve housing and divides an interior of the valve housing into a first chamber and a second chamber,
- the switch element is pre-tensioned by at least one pre-tensioning element arranged in the switch valve,
- the prosthetic knee joint comprises at least one spring element that applies a counter-force to the switch element, which is oriented against the pre-tension.

Such a prosthetic knee joint is known from DE 10 2018 111441 A1.

Prosthetic knee joints have been known from the prior art for many years. They are important components of leg prostheses and should imitate the functions of a human leg as naturally as possible. In this context, a human knee is able to allow movements in some situations and to block them in others. This is important in order to provide the required stability whenever possible. The versatility of the human knee presents a challenge for a prosthetic knee. To be able to perform movements at different speeds and with different degrees of damping, prosthetic knees are often equipped with a hydraulic system. A prosthetic knee in which a hydraulic system is installed usually has two hydraulic chambers, a so-called extension chamber and a flexion chamber, which are fluidically connected to each other. For this purpose, at least one connecting line is provided. Both chambers contain a piston that can move inside the chamber and thus alter the volume of the respective chamber. It can be designed as a single piston. In this case, the two chambers are arranged on two opposite sides of the piston, which is preferably designed as a rotary piston. This causes the volume of the one chamber to reduce when the volume of the respective other chamber increases. Of course, two pistons can also each be arranged in a cylinder and each limit one chamber in the respective cylinder.

The joint upper part is mounted relative to the joint lower part such that it can be pivoted about a pivot axis.

The flexion describes a bending of the knee, i.e. a movement of the joint upper part relative to the joint lower part in a first direction, referred to as the flexion direction. During this movement, hydraulic liquid, for example a hydraulic oil, flows from the flexion chamber into the extension chamber. During the reverse movement, referred to as extension, the knee joint is extended. In the process, the hydraulic liquid flows from the extension chamber into the flexion chamber. In this case, the extension chamber is the chamber in which the pressure increases during extension, and the flexion chamber is the chamber in which the pressure increases during flexion.

The speed at which the hydraulic fluid moves from the one chamber into the other chamber is decisive for the speed of the movement of the joint, i.e. the movement of the joint upper part relative to the joint lower part. It depends, among other things, on the flow cross-section of the connection line. DE 693 12 771 T1 discloses a device that can be used to control a hydraulic system in an upper leg prosthesis.

Different speeds are advantageous at different phases in the gait cycle, so that a switch valve is integrated into the prosthetic knee joint. It is thus possible, for example, to switch between two different connection lines with different flow cross-sections and therefore different flow resistances. The switch valve features a valve housing in which a switch element is located. The switch element is designed, for example, as a displaceable piston or slide. The switch element is a component which, by displacing it into a first position or into a second position, can change a flow cross-section or a flow velocity within the hydraulic system and/or can open or close a hydraulic line or fluid connection. The valve housing is the component of the prosthetic knee joint in which the switch element can be displaced into the first and second position. It can also be designed as a separate component. Alternatively, another component of the prosthetic knee joint, such as the joint lower part or the joint upper part, can form the valve housing. For this purpose, a cavity or a bore is provided in the respective component, for example, in which the switch element moves.

This switch element can be brought into a first position and into a second position relative to the valve housing. When in the first position, the valve is in a first state which, for example, opens a first connection line. In a preferred embodiment, this connection line has a high flow resistance, so that the movement of the knee joint is heavily damped. As a result, only a slow and load-bearing movement of the joint upper part relative to the joint lower part is possible, which is advantageous, for example, in the stance phase while walking, when sitting down, or descending stairs or a slope.

If, however, the switch element is brought into the second position relative to the valve housing, the switch valve is in a second state in which another path is opened for the hydraulic liquid. This may be a second connection line, for example. Preferably, the damping of the movement of the knee joint in this state of the valve is weaker, which can be achieved, for example, by the second connection line having a lower flow resistance than the first connection line. This second state is advantageous in the swing phase of a step, for example, as in this phase the knee does not bear any load and heavy damping would in this case be unphysiological.

The switch element of a prosthetic knee joint according to the preamble divides the interior of the valve housing into a first chamber and a second chamber. The switch element is preferably located completely inside the valve housing and is preferably completely surrounded by the respective hydraulic fluid.

To be able to move the switch element from the first position into the second position and thus switch the switch valve, an actuation mechanism is preferably provided, by means of which a force can be applied to the switch element. The switch element is pre-tensioned by at least one pre-tensioning element, for example in the form of a spring, particularly a coil spring. The pre-tension is preferably directed towards the first position of the switch element, which causes the stronger damping.

The first position of the switch element relative to the valve housing can depend on a large number of parameters. Among other factors, it can depend on the magnitude of the pre-tension, the hydraulic pressure in the hydraulic system, possible flow paths that the hydraulic liquid can take through the system, particularly from one chamber to the other, the general dimensions of the prosthesis, especially the prosthetic knee, the type of prosthetic knee, to name but a few parameters. The exact determination of the first position of the switch element relative to the valve housing is, however, very significant, as it determines the displacement path required along which the switch element must be displaced in order to go from the first position into the second position. As such, it also determines how quickly the switch valve reacts and, for example, at which point in a step cycle the switch valve is switched from the first state, in which the switch element is in the first position, into the second state. However, the pre-tensioning element is unfortunately only located inside the valve and therefore mostly inside the hydraulic system and often in the hydraulic liquid, so that it is difficult or even impossible to access. The remaining parameters are often not obtained until assembly of the knee joint and are difficult or impossible to determine beforehand. The adjustment of the first position of the switch element relative to the valve housing is therefore barely possible or only with considerable effort.

The prosthetic knee joint also has a spring element, which is also configured to apply a force, namely the counter-force, to the switch element. This can happen directly, for example by the spring element being in mechanical contact with the switch element, or indirectly, by the spring element transmitting the force to an intermediate component and the force being transmitted from there directly or indirectly to the switch element. If no further force is applied to the spring element, thus strengthening the counter-force, the pre-tension is greater than the counter-force and the switch element is in the first position. In this position, the flow resistance that counters the flow of the hydraulic liquid through the hydraulic system and in particular through the switch valve is greater than in the second position of the switch element. As such, the standard setting of the valve ensures a high resistance that opposes a pivoting of the joint upper part relative to the joint lower part.

If an external force is applied to the spring element that enhances the counter-force, it can overcome the pre-tension and displace the switch element from the first position into the second position. If the external force decreases at a later point in time or disappears completely, the counter-force also reduces so that it is once again smaller than the pre-tension. The pre-tension then displaces the switch element back into the first position. The greater the overall force resulting from pre-tension and counter-force, the faster this happens.

The invention therefore aims to improve a prosthetic knee joint in such a way that a first position suitable for controlling the knee joint can be easily achieved.

The invention solves the addressed task by way of a prosthetic knee joint according to the preamble of claim 1, characterized in that, within the valve housing and/or the switch element, at least one fluid connection is arranged between the first chamber and the second chamber. If, for example, an external force is now applied to the spring element that opposes the pre-tension of the pre-tensioning element, the spring element is preferably tensioned, particularly compressed, and thus charged with potential energy. As a result, it exerts a force on the switch element. This can occur directly by, for example, an end of the spring element resting on the switch element, or indirectly by the spring element initially transmitting its force to one or multiple further components of the prosthetic knee joint, which transfer the force directly or indirectly to the switch element.

If the switch element is to avoid this force, it must be displaced against the pre-tension of the pre-tensioning element. As a result, one of the two chambers within the valve housing becomes smaller and the other chamber becomes larger. At least part of the hydraulic liquid must therefore leave the chamber that reduces in size. At the same time, hydraulic liquid has to flow into the chamber that increases in size. The at least one fluid connection between the first chamber and the second chamber is provided for this purpose, said connection being located, according to the invention, inside the valve housing. The cross-section of the at least one fluid connection is decisive for the amount of hydraulic fluid that flows from the reducing chamber, through the fluid connection and into the enlarging chamber. Due to the fact that the fluid connection, which can also be referred to as a bypass, is arranged inside the valve housing, no additional installation space is required, which is usually limited in prosthetic knee joints. Preferably, multiple, for example at least three, fluid connections are provided. The fluid connections can be designed to be identical. For example, they are the same length and/or have the same cross-section, for example circular or polygonal, and/or the same cross-sectional area, preferably less than 1 $mm^2$, especially preferably less than 0.5 $mm^2$ and especially preferably less than 0.385 $mm^2$. Preferably, they generate the same flow resistance. This does not necessarily require an identical length or an identical cross-section or an identical cross-sectional area, but it is advantageous. The fluid connections can also be designed to be different and, for example, generate flow resistances that are not identical.

If the valve is to be switched, a force must be applied to the switch element and the latter moved from the first position into the second position or vice-versa. According to the invention, the movement of the switch element inside the valve housing is damped due to the interior of the valve housing being divided into two chambers by the switch element, the two chambers being filled with hydraulic fluid. To move the switch element, it is therefore necessary to guide fluid from the one chamber into the other chamber. This is only possible through the fluid connection, regardless of the switch state of the valve, i.e. the position of the switch element, so that the cross-section of this connection is decisive for the speed at which the switch element can react to an external force impact.

The damping of this reaction means that brief force impacts, which should not usually lead to a change in the switch state of the valve, do not persist for long enough to transfer a sufficient amount of the fluid between the two chambers inside the valve housing in this time and to switch the valve.

In a preferred embodiment, the multiple fluid connections are designed in such a way that they are effective in different positions of the switch element. To this end, multiple indentations, such as notches, grooves or flutes, are arranged in the inner wall of the valve housing, which is preferably in contact with the switch element. These indentations preferably differ in length. On the one hand, this can mean that such an indentation is closed by the switch element moving from the first position into the second position. On the other hand, such a fluid connection can also be opened by the moving switch element.

To ensure that an indentation in the inner wall of the valve housing can form a fluid connection between the first chamber and the second chamber, one end of the indentation must lie in the area of the inner wall that limits the first chamber and the other end in the area of the inner wall that limits the second chamber. When the switch element is displaced from the first position into the second position or vice-versa, the one chamber gets bigger and the other smaller. This also causes the parts of the inner wall that limit the first chamber and the second chamber to change.

Preferably, at least one fluid connection extends through the switch element. Particularly preferably, the at least one fluid connection is a bore arranged in a surface of the switch element that is perpendicular to the direction of displacement of the switch element. Preferably, multiple identical or differently designed fluid connections are provided. Alternatively or additionally, indentations are preferably arranged on the outside of the switch valve.

Alternatively or additionally, at least one fluid connection extends through the valve housing. Particularly preferably, such a fluid connection is arranged as an indentation, notch or channel in a wall of the valve housing that limits the interior of the valve housing. In this embodiment, the cross-section of the fluid connection is also decisive for the amount of fluid that is pushed by the force exerted by the spring element from the reducing chamber into the enlarging chamber.

Alternatively or additionally, at least one fluid connection extends between the valve housing and the switch element.

Irrespective of the design and/or number of the fluid connections provided, the smaller the overall cross-section of all available fluid connections, the greater the resistance to movement of the switch element due to the flow resistance of the at least one fluid connection.

If the switch element is in the first position, the hydraulic system provides a large resistance to a movement of the joint lower part relative to the joint upper part. In this state, the movement is heavily damped. In the second state of the switch valve, the switch element is in the second position and the movement of the joint lower part relative to the joint upper part is gently damped. The prosthetic knee joint also comprises at least one spring element that applies a counter-force to the switch element, which is oriented against the pre-tension.

Preferably, the cross-section of at least one fluid connection, preferably all fluid connections, cannot be changed and/or the respective fluid connection, preferably all fluid connections, cannot be closed.

The at least one spring element is preferably arranged in such a way that the switch element can be brought from the first position into the second position by applying a force to the at least one spring element for at least a predetermined period of time. Particularly preferably, the switch element cannot be brought from the first position into the second position by applying a force to the spring element for less than the predetermined time period. This embodiment means that a brief force impact, which is shorter than the predetermined time period, does not cause the switch element to move from the first position into the second position. Such a force impact can occur, for example, when the wearer of the prosthetic knee joint trips or bumps into an object. This usually happens during the swing phase, i.e. when the foot that is connected to the wearer's body via the prosthetic knee joint is not in contact with the ground. As a result of the force impact, the at least one spring element is compressed and thus charged with energy. For example, the force impact is applied to the spring pin of the cartridge in which the at least one spring element is arranged. As soon as the force is no longer applied, the stored energy discharges and the spring pin moves back into the starting position. In this case, the time in which the at least one spring element is charged with mechanical energy is too short to displace the switch element far enough to reach the second position. It should be noted that this does not mean that the switch element is not moved. A movement can occur, but it does not lead to the second position being reached.

Preferably, a force must be exerted on the at least one spring element in order to bring the switch element from the first position into the second position. There is preferably no other way to move the switch element.

To reduce noise that may occur, in particular, when one component, for example a spring sleeve, strikes another component, such as the cover of the spring cabinet or the spring housing, at least one bushing is arranged between two respective components that come into contact with each other in this manner, said bushing preferably being made of a plastic, especially a thermoplastic material. For example, the polyoxymethylene group, often shortened to POM, is well-suited to this.

Particularly preferably, the prosthetic knee joint is or can be produced according to one of the methods described here. In particular, the counter-force applied by the at least one spring element is preferably set.

Figure 2:
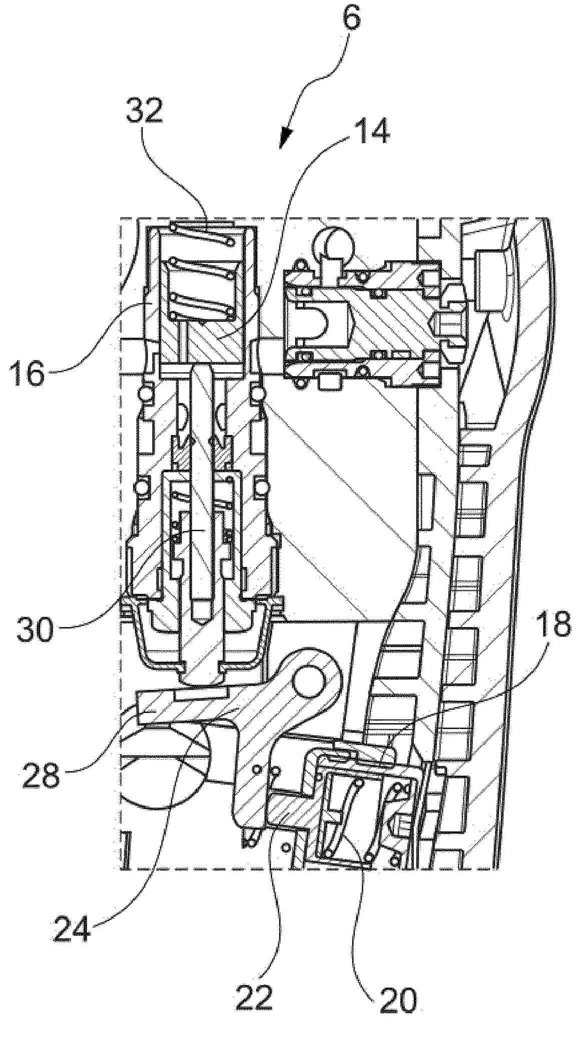
Figure 3:
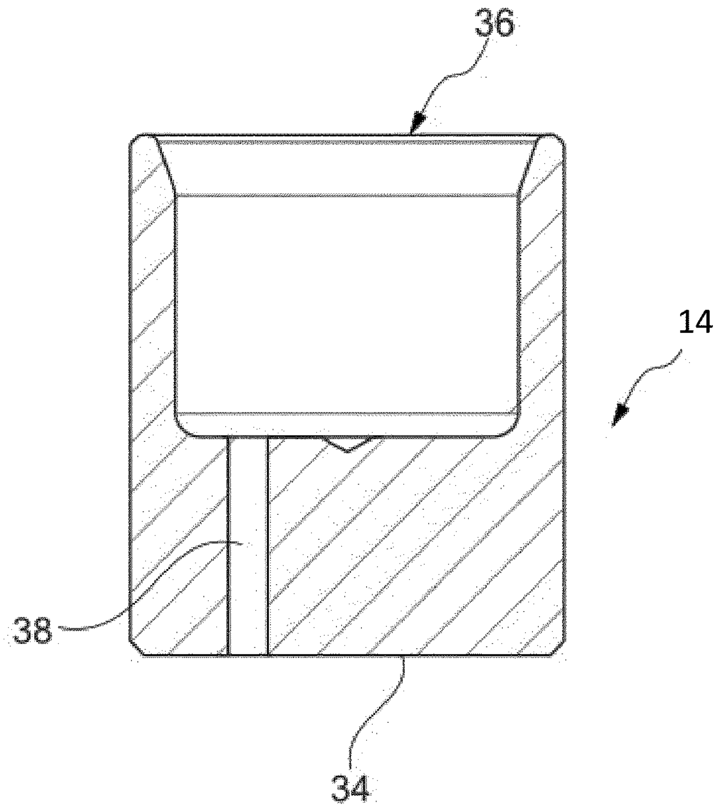
Figure 4:
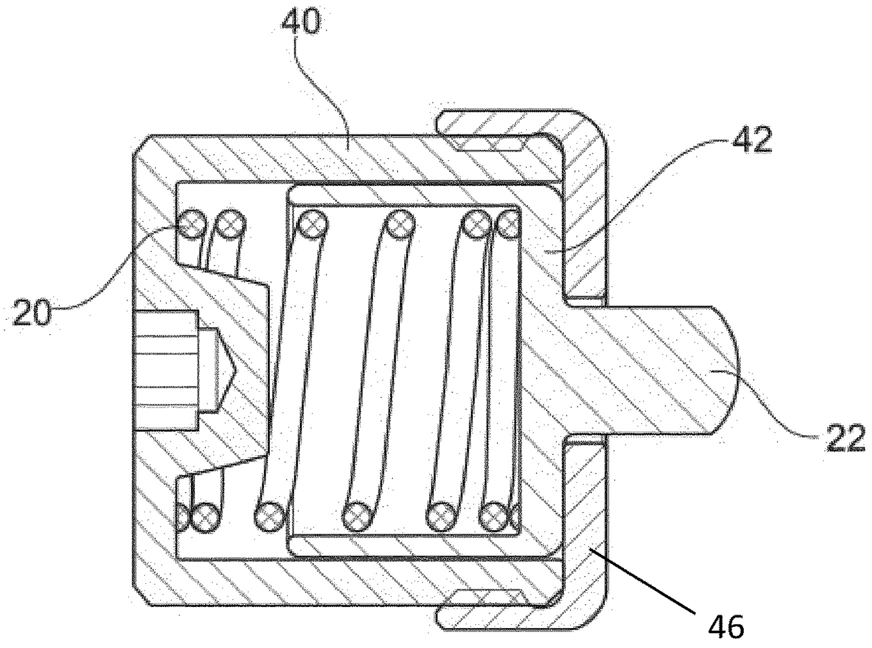
Figure 5:
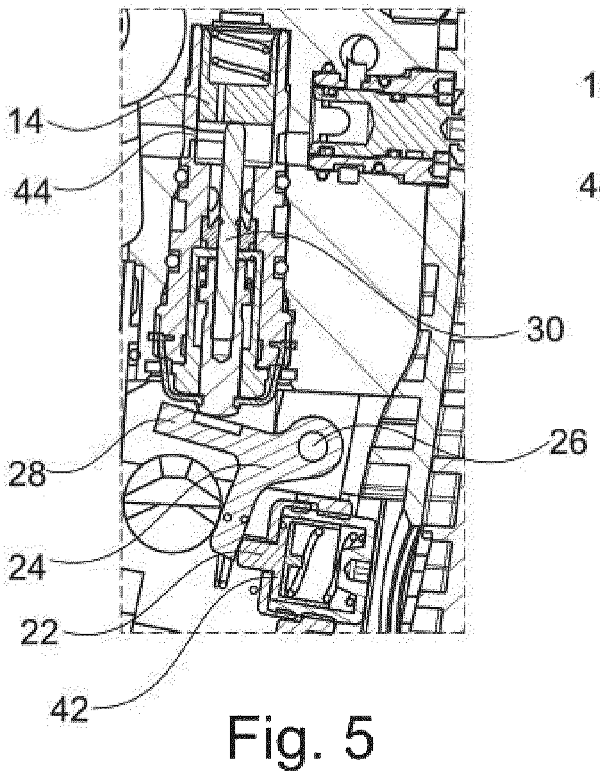
Figure 6:
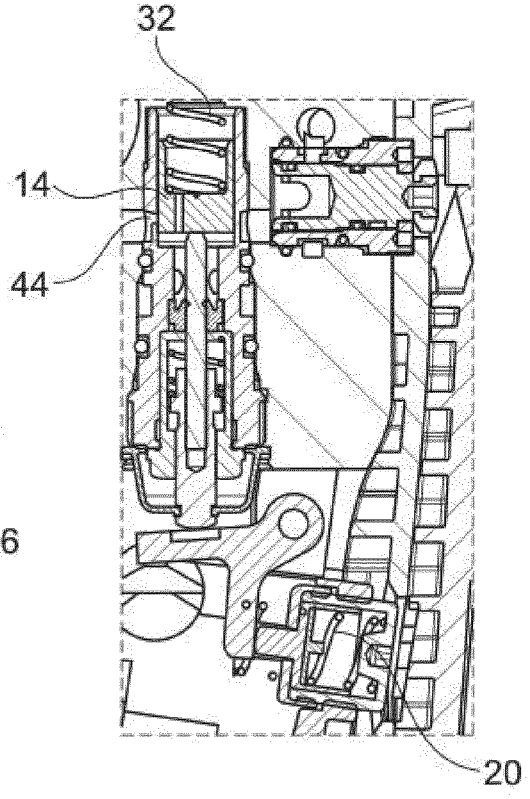
Figure 7:
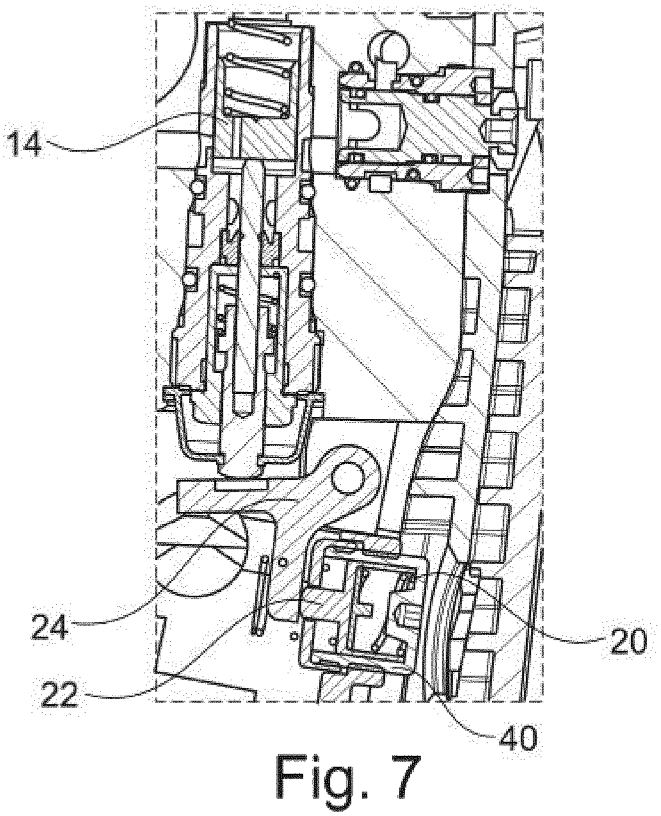
Figure 8:
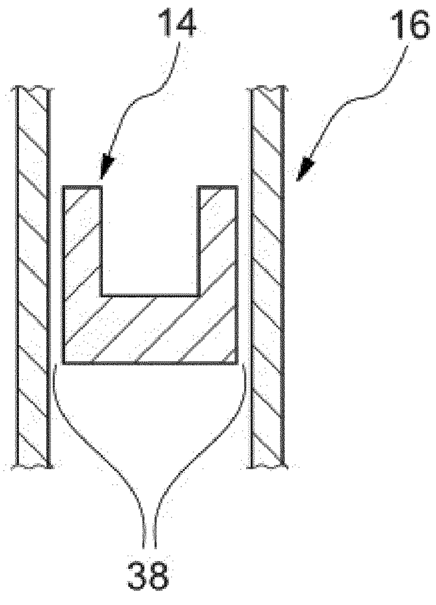
Figure 9:
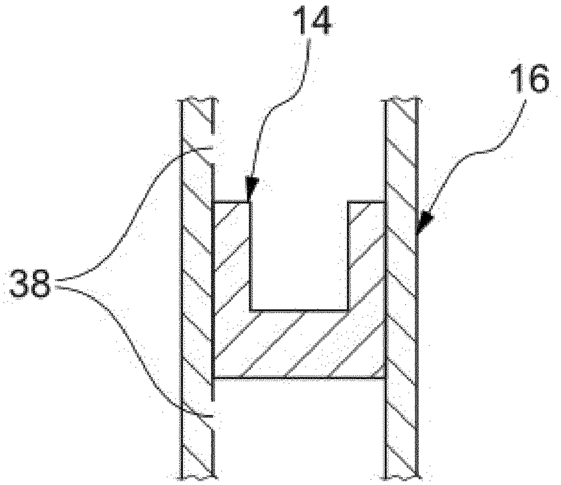
Figure 10:
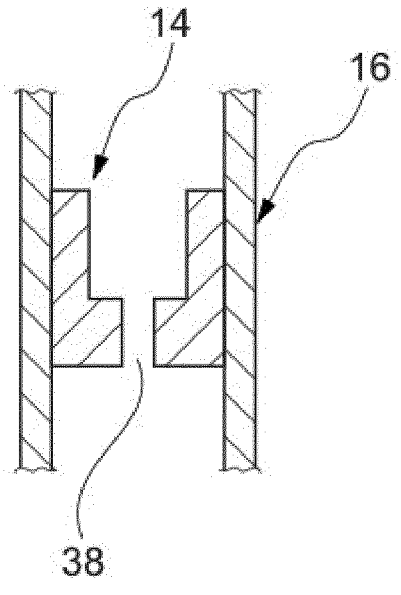
Figure 11:
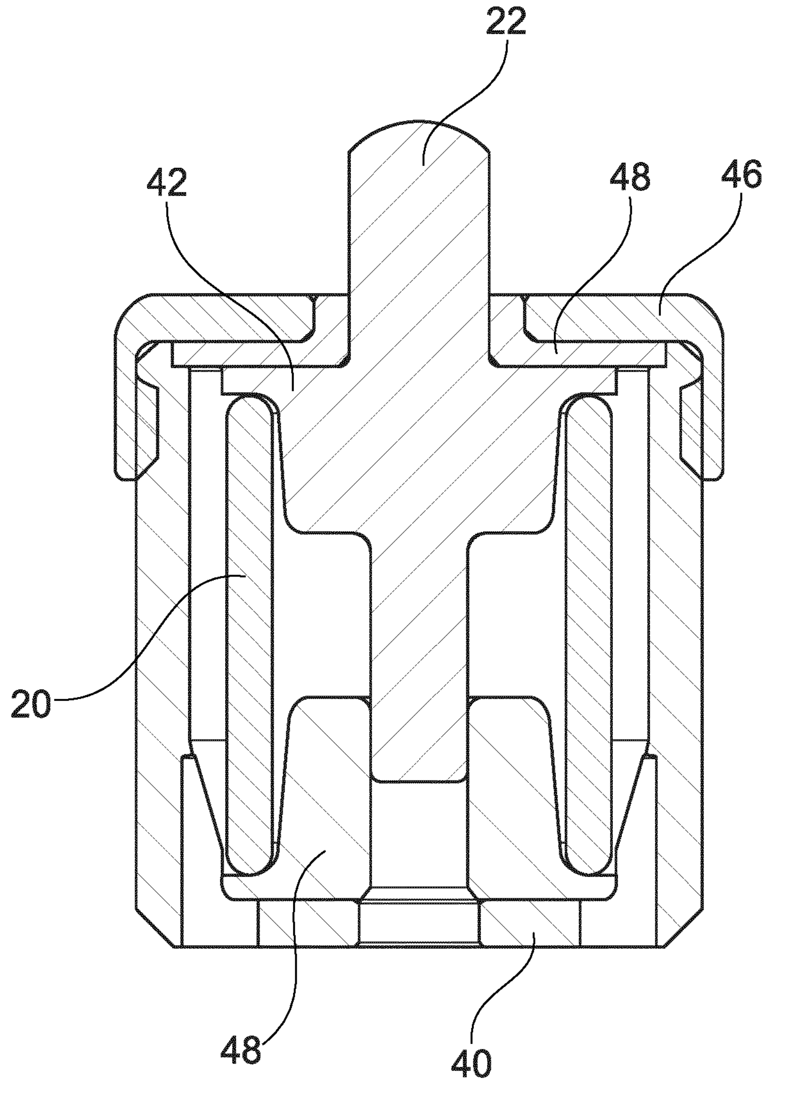

In the following, an embodiment example of the invention will be explained in more detail with the aid of the accompanying figures. They show:

FIG. 1—a schematic sectional view through a prosthetic knee joint according to an embodiment example of the present invention, FIG. 2—an enlarged section from FIG. 1, FIG. 3—a switch element for a switch valve, FIG. 4—a spring cartridge for a prosthetic knee joint, FIGS. 5 to 7—enlarged sections from the sectional view according to FIG. 1 with the switch element in different positions, FIGS. 8 to 10—schematic representations of different arrangements of the fluid connection and FIG. 11—a schematic representation of a further spring cartridge.

FIG. 1 shows the schematic sectional view through a prosthetic knee joint that comprises a joint lower part 2, a joint upper part 4 and a hydraulic system that contains a switch valve 6. The hydraulic system comprises a flexion chamber 8 and an extension chamber 10 that are fluidically connected to each other. During an extension, i.e. stretching, of the knee, the hydraulic fluid flows from the extension chamber into the flexion chamber 8. On the other hand, during the flexion, i.e. bending, of the knee, the hydraulic fluid flows from the flexion chamber 8 into the extension chamber 10. Both chambers 8, 10 are separated from each other by a piston 12, designed as a swivel piston in the embodiment example. If the piston 12 moves, one of the two chambers 8, 10 becomes bigger and the other of the two chambers 10, 8 becomes smaller.

On the way from the extension chamber 10 into the flexion chamber 8 and/or vice-versa, the hydraulic fluid also flows through the switch valve 6. The switch valve 6 has a switch element 14, which can be brought into a first position and into a second position.

FIG. 2 shows an enlarged section from FIG. 1, in which the switch valve 6 is depicted in greater detail. In the embodiment example shown, the switch element 14 is situated completely in the hydraulic fluid and is moveably mounted inside a valve housing 16. To this end, a force and/or a torque is applied to an external component 18, which causes a spring element 20 to compress. It is located in a spring cartridge, which shall be discussed in more detail later. This spring cartridge features a spring pin 22, which is moved by a force that is applied by the pre-compressed spring element 20. The spring pin 22 transfers this force to a deflection lever 24, which is arranged such that it can be pivoted about a deflection axis 26. An arm 28 of the deflection lever 24 rests on a valve pin 30, which is moved upwards by the arm 28, thereby moving the switch element 14. The switch element 14 is thus displaced from the first position into the second position.

The switch element 14 is pre-tensioned via a pre-tensioning element 32. In the embodiment example shown, the pre-tensioning element 32 is designed as a compression spring and pushes the switch element 14 downwards. The pre-tensioning of the pre-tensioning element 14 thus opposes, among other things, a force applied by the spring pin 22. Depending on which of the two forces is greater, the switch element 14 moves into the first or the second position.

FIG. 3 shows a sectional view through the switch element 14. When in the installed state, the valve pin 30 rests on its underside 34. In the embodiment example shown, at the opposite end the switch element 14 there is an indentation 36, in which the pre-tensioning element 32 rests when in the installed state. A fluid connection 38 extends through the switch element 14 by means of which the volume above the switch element 14 is fluidically connected to the volume below the switch element 14. If the switch element 14 is displaced inside the valve housing 16, hydraulic fluid flows through this fluid connection 38.

FIG. 4 depicts the spring cartridge in which the spring element 20 is located. In the embodiment example shown, this spring element 20 is also designed as a compression spring. It is located in a spring housing 40, in which there is a spring sleeve 42 that is arranged such that it can be displaced relative to the spring housing 40. The spring pin 22 is arranged on the spring sleeve 42. The spring sleeve 42 is arranged such that it can be displaced relative to the spring housing 40, which comprises a spring cabinet cover 46, wherein the spring pin 22 protrudes through its opening.

FIG. 5 shows the representation of the spring cartridge with a spring pin 22 moved to the left. The spring pin 22 is in the initial state and the spring 20 is not compressed. As a result, the deflection lever 24 is pivoted about the deflection axis 26, so that the arm 28 displaces the valve pin 30 and thus the switch element 14 upwards. The switch element 14 thus frees an opening 44, thereby reducing a flow resistance that opposes the hydraulic fluid between the two chambers 8, 10.

In FIG. 6, the spring element 20 is relaxed and exerts no or only a small force. The force exerted by the pre-tensioning element 32 is greater, so that the switch element 14 is pushed downwards. This closes the opening 44 and a flow of hydraulic fluid through this opening 44 is prevented.

FIG. 7 depicts the arrangement from FIGS. 5 and 6, wherein the spring element is compressed. This occurs, for example, due to an external force acting on the spring element 20 and/or the spring housing 40. Compared to the representations from FIG. 6, the spring housing 40 is displaced to the left, so that the spring pin 22 no longer protrudes so far out of the spring housing. It should be noted that, compared to the representations in FIG. 6, in the representation shown in FIG. 7 the spring pin 22 has not been displaced relative to further components of the prosthetic knee joint. In particular, the deflection lever 24 has not been pivoted either, so that the switch element 14 has also not moved. The force acting on the spring element 20 is therefore only exerted for a very short period of time. If the force is only briefly exerted and then quickly significantly reduces again or disappears, the spring element relaxes again, without the switch element 14 being displaced. Brief force impacts are thus absorbed without it resulting in an opening of the valve.

FIGS. 8 to 10 show various options for arranging the fluid connection 38. In each figure, the valve housing 16 is depicted with the movably arranged switch element 14 therein. In FIG. 8 there is a ring-shaped fluid connection 38 between the valve housing 16 and the switch element 14. FIG. 9 shows a fluid connection 38 that extends through the valve housing 16 and FIG. 10 a fluid connection that extends through the switch element 14.

FIG. 11 shows a further embodiment of a spring cartridge with the spring cabinet cover 46 and the spring sleeve 42 on which the spring pin 22 is arranged. The spring is only schematically depicted. Between the spring cabinet cover 46 and the spring sleeve 42 is a bushing 48, which preferably consists of or is made of a plastic, for example a thermoplastic. Such a bushing 48 is also located between the lower end of the spring sleeve 42 and the spring housing 40. The two bushings 48 serve particularly to reduce noise.

REFERENCE LIST

2 joint lower part
4 joint upper part
6 switch valve
8 flexion chamber
10 extension chamber
12 piston
14 switch element
16 valve housing
18 external component
20 spring element
22 spring pin
24 deflection lever
26 deflection axis
28 arm
30 valve pin
32 pre-tensioning element
34 underside
36 indentation
38 fluid connection
40 spring housing
42 spring sleeve
44 opening
46 spring cabinet cover
48 bushing

The invention claimed is:

1. A prosthetic knee joint, comprising: with
a joint lower part;
a joint upper part;
a hydraulic system, wherein the hydraulic system comprises
an extension chamber,
a flexion chamber, and
at least one piston, wherein movement of the at least one piston causes a volume of the extension chamber and/or the flexion chamber to change,
wherein the hydraulic system comprises at least one switch valve, and the at least one switch valve comprises
a valve housing, and
a switch element movably mounted within the valve housing, wherein the switch element can be brought into a first position and into a second position within the valve housing, and wherein the switch element divides an interior of the valve housing into a first chamber and a second chamber,
wherein the switch element is pre-tensioned by at least one pre-tensioning element arranged in the at least one switch valve; and at least one spring element that applies a counter-force to the switch element, which is oriented against a pre-tension from the at least one pre-tensioning element, wherein, within the valve housing and/or the switch element, at least one fluid connection is arranged between the first chamber and the second chamber.

2. The prosthetic knee joint according to claim 1, wherein the at least one fluid connection extends through the switch element.

3. The prosthetic knee joint according to claim 1, wherein the at least one fluid connection extends through the valve housing.

4. The prosthetic knee joint according to claim 1, wherein the at least one fluid connection extends between the valve housing and the switch element.

5. The prosthetic knee joint according to claim 1, wherein a cross-section of the at least one fluid connection cannot be changed and/or a fluid connected to the at least one fluid connection cannot be closed.

6. The prosthetic knee joint according to claim 1, wherein the at least one spring element is arranged in such a way that the switch element can be brought from the first position into the second position by applying a force to the at least one spring element for at least a predetermined period of time.

7. The prosthetic knee joint according to claim 6, wherein the switch element cannot be brought from the first position into the second position by applying a force to the at least one spring element for less than the predetermined time period.

* * * * *